United States Patent [19]
Moro et al.

[11] Patent Number: 6,017,533
[45] Date of Patent: Jan. 25, 2000

[54] PEPTIDES HAVING SPECIFIC AFFINITY TO PITUITARY ADENYLATE CYCLASE ACTIVATING POLYPEPTIDE TYPE 1 RECEPTORS

[75] Inventors: Osamu Moro, Lexington, Mass.; Kawori Wakita, Yokohama; Manami Ohnuma, Kamakura, both of Japan; Ethan A. Lerner, Newton, Mass.; Masahiro Tajima, Yokohama, Japan

[73] Assignees: Shiseido Company, Ltd., Tokyo, Japan; The General Hospital Corporation, Boston, Mass.

[21] Appl. No.: 08/637,437

[22] Filed: Apr. 25, 1996

[51] Int. Cl.[7] .................. A61K 39/00; G01N 33/567; C07K 2/00; C07K 5/00
[52] U.S. Cl. ................ 424/185.1; 435/7.21; 436/503; 530/300; 530/324; 530/350
[58] Field of Search ............... 435/7.21; 530/300, 530/324, 350; 424/185.1; 436/503

[56] References Cited

U.S. PATENT DOCUMENTS 5,637,309   6/1997   Tajima et al. .

FOREIGN PATENT DOCUMENTS 9504829   2/1995   WIPO .

*Primary Examiner*—Anthony C. Caputa
*Assistant Examiner*—Mark Navarro
*Attorney, Agent, or Firm*—Wenderoth, Lind & Ponack, L.L.P.

[57] ABSTRACT

This specification relates to the use of peptides having a specific affinity to pituitary adenylate cyclase activating polypeptide (PACAP) receptors, particularly MAX (67 amino acids), NSP (61 amino acids) and M65 (46 amino acids). MAX and NSP act as agonists to PACAP type 1 receptors, and M65 acts as an antagonist to PACAP type 1 receptors.

17 Claims, 5 Drawing Sheets

SEQUENCE LISTING (1) GENERAL INFORMATION:

(iii) NUMBER OF SEQUENCES: 7

(2) INFORMATION FOR SEQ ID NO: 1:

(i) SEQUENCE CHARACTERISTICS:
      (A) LENGTH: 67 amino acids
      (B) TYPE: amino acid
      (C) STRANDEDNESS: single
      (D) TOPOLOGY: linear (ii) MOLECULE TYPE: peptide (xi) SEQUENCE DESCRIPTION: SEQ ID NO: 1:

Gly Ser Ile Leu Cys Asp Ala Thr Cys Gln Phe Arg Lys Ala Ile Asp
1               5                   10                  15

Asp Cys Gln Lys Gln Ala His His Ser Asn Val Leu Gln Thr Ser Val
            20                  25                  30

Gln Thr Thr Ala Thr Phe Thr Ser Met Asp Thr Ser Gln Leu Pro Gly
            35                  40                  45

Asn Ser Val Phe Lys Glu Cys Met Lys Gln Lys Lys Lys Glu Phe Lys
        50                  55                  60

Ala Gly Lys
65

(2) INFORMATION FOR SEQ ID NO: 2:

(i) SEQUENCE CHARACTERISTICS:
        (A) LENGTH:  61 amino acids
        (B) TYPE:  amino acid
        (C) STRANDEDNESS: single
        (D) TOPOLOGY:  linear (ii) MOLECULE TYPE:  peptide (xi) SEQUENCE DESCRIPTION:  SEQ ID NO: 2:

Gly Ser Gly Gln Phe Arg Lys Ala Ile Asp Asp Cys Gln Lys Gln Ala
1               5                   10                  15

His His Ser Asn Val Leu Gln Thr Ser Val Gln Thr Thr Ala Thr Phe
            20                  25                  30

Thr Ser Met Asp Thr Ser Gln Leu Pro Gly Asn Ser Val Phe Lys Glu
            35                  40                  45

Cys Met Lys Gln Lys Lys Lys Glu Phe Lys Ala Gly Lys
        50                  55                  60

(2) INFORMATION FOR SEQ ID NO: 3:

(i) SEQUENCE CHARACTERISTICS:
        (A) LENGTH:  46 amino acids
        (B) TYPE:  amino acid
        (C) STRANDEDNESS: single
        (D) TOPOLOGY:  linear (ii) MOLECULE TYPE:  peptide (xi) SEQUENCE DESCRIPTION:  SEQ ID NO: 3:

Gly Ser Cys Asp Ala Thr Cys Gln Phe Arg Lys Ala Ile Asp Asp Cys
1               5                   10                  15

Gln Lys Gln Ala His His Ser Asn Val Pro Gly Asn Ser Val Phe Lys
            20                  25                  30

Glu Cys Met Lys Gln Lys Lys Lys Glu Phe Lys Ala Gly Lys
            35                  40                  45

(2) INFORMATION FOR SEQ ID NO: 4:

(i) SEQUENCE CHARACTERISTICS:
        (A) LENGTH:  38 amino acids
        (B) TYPE:  amino acid
        (C) STRANDEDNESS: single
        (D) TOPOLOGY:  linear (ii) MOLECULE TYPE:  peptide (xi) SEQUENCE DESCRIPTION:  SEQ ID NO: 4:

His Ser Asp Gly Ile Phe Thr Asp Ser Tyr Ser Arg Tyr Arg Lys Gln
1               5                   10                  15

-continued

```
Met Ala Val Lys Lys Tyr Leu Ala Ala Val Leu Gly Lys Arg Tyr Lys
            20                  25                  30

Gln Arg Val Lys Asn Lys
            35
```

(2) INFORMATION FOR SEQ ID NO: 5:

(i) SEQUENCE CHARACTERISTICS:
        (A) LENGTH: 27 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 5:

```
His Ser Asp Gly Ile Phe Thr Asp Ser Tyr Ser Arg Tyr Arg Lys Gln
1               5                   10                  15

Met Ala Val Lys Lys Tyr Leu Ala Ala Val Leu
            20                  25
```

(2) INFORMATION FOR SEQ ID NO: 6:

(i) SEQUENCE CHARACTERISTICS:
        (A) LENGTH: 33 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 6:

```
Phe Thr Asp Ser Tyr Ser Arg Tyr Arg Lys Gln Met Ala Val Lys
1               5                   10                  15

Lys Tyr Leu Ala Ala Val Leu Gly Lys Arg Tyr Lys Gln Arg Val
            20                  25                  30

Lys Asn Lys
```

(2) INFORMATION FOR SEQ ID NO: 7:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 7:

```
Phe Thr Asp Ser Tyr Ser Arg Tyr Arg Lys Gln Met Ala Val Lys
1               5                   10                  15

Lys Tyr Leu Ala Ala Val Leu
            20
```

PEPTIDES HAVING SPECIFIC AFFINITY TO PITUITARY ADENYLATE CYCLASE ACTIVATING POLYPEPTIDE TYPE 1 RECEPTORS

BACKGROUND OF THE INVENTION

1. Field of the Invention

This invention relates to technical fields relating to actions on pituitary adenylate cyclase activating polypeptide (hereinafter referred to as "PACAP") receptors. More specifically, the invention relates to use of peptides having a specific affinity to PACAP subtype 1 receptors.

2. Description of Related Art

PACAP was isolated from the hypothalami of sheep as a peptide activating adenylate cyclase (see, *Biochem. Biophys. Res. Commun.*, 567–574 (1989); Arimura, A, et al., *Regul. Peptides*, 37, 287–303 (1992)). The amino acid sequence of PACAP is identified as follows (this is hereinafter referred to as "PACAP 38").

```
His Ser Asp Gly Ile Phe Thr Asp Ser Tyr Ser Arg Tyr Arg Lys Gln   (SEQ ID NO: 4-NH2)
1               5                   10                  15

Met Ala Val Lys Lys Tyr Leu Ala Ala Val Leu Gly Lys Arg Tyr Lys
            20                  25                  30

Gln Arg Val Lys Asn Lys-NH2
            35
```

Thereafter, the existence of PACAP 27 consisting of the following shorter amino acid sequence at the N-terminal side was revealed:

```
His Ser Asp Gly Ile Phe Thr Asp Ser Tyr Ser Arg Tyr Arg Lys Gln   (SEQ ID NO: 5-NH2)
1               5                   10                  15

Met Ala Val Lys Lys Tyr Leu Ala Ala Val Leu-NH2
            20                  25
```

These PACAPs are considered to be members belonging to the secretin/glucagon/VIP family because in a comparison of amino acid sequences, homology of about 68% is observed between these PACAPs and the amino acid sequence composed of 28 amino acid residues at the N-terminal side of VIP.

Since PACAP exhibits homology to VIP as mentioned above, it was suggested that it signaled through receptors analogous to VIP receptors. It is now known that at least three subtypes of PACAP receptors exist. PACAP exhibits affinity but VIP does not exhibit affinity to PACAP type 1 receptors, while both PACAP and VIP exhibit affinity to PACAP type 2 and PACAP type 3 receptors. PACAP type 2 receptors and PACAP type 3 receptors are also called VIP type 1 receptors and VIP type 2 receptors, respectively.

PACAP is widely distributed in the body, for example, central nervous systems, testes, ovaries, adrenals, lungs, digestive tracts, pancreas, etc., and its action is considered to range widely. As to the PACAP receptors, it is recognized that the type 1 is expressed at a high level in brains, but at a low level at adrenals and scarcely at other principal tissues, whereas the type 2 is recognized to be expressed in lungs, brains, small intestines, livers, etc. and the type 3 is recognized to be expressed in lungs, stomachs, small intestines, pancreas, etc. As is seen from the above, it is known that some specificity exists in the tissue distribution of the PACAP receptors.

Agonists or antagonists having specific affinity only to the type 1 PACAP receptor have not yet been disclosed in technical literatures. Therefore, for determining, at the present point in time, whether or not targeted receptors among subtypes of PACAP receptors are type 1, a binding test wherein at least PACAP 38 or PACAP 27, and VIP are used in combination as ligands, etc. must be used.

Therefore, provision of compounds exhibiting specific affinity (or binding) to PACAP type 1 receptors will be desired even for merely examining functions of PACAP receptors.

On the other hand, part of the present inventors revealed that maxadilan derived from the salivary gland of *Lutzomyia longipalpis,* and its mutants, when infected into the epidermis of animals, cause erythema without itch and pain, and are extremely interesting peptides (see, for example, WO 91/00293; E. A. Lerner et al., *J. Bio. Chem.* 267, 1062–1066 (1992)). Further, they also revealed that a peptide (hereinafter referred to as "MAX") represented by the following amino acid sequence, among the mutants, exhibits a stronger erythema-forming action than natural maxadilan (see, for example, U.S. Pat. No. 5,480,864).

```
Gly Ser Ile Leu Cys Asp Ala Thr Cys Gln Phe Arg Lys Ala Ile Asp 16   (SEQ ID NO: 1)
1               5                   10                  15

Asp Cys Gln Lys Gln Ala His His Ser Asn Val Leu Gln Thr Ser Val 32
            20                  25                  30

Gln Thr Thr Ala Thr Phe Thr Ser Met Asp Thr Ser Gln Leu Pro Gly 48
            35                  40                  45

Asn Ser Val Phe Lys Glu Cys Met Lys Gln Lys Lys Glu Phe Lys 64
            50                  55                  60

Ala Gly Lys                                                     67
65
```

They still further revealed that other various mutants of maxadilan also exhibit maxadilan-like biological activities, and part of them have agonistic binding ability to the surfaces of the cell membranes of tissues, particularly tissues derived from brains of mammals, and the other part have antagonistic binding ability thereto (see, U.S. Ser. No. 08/540,033).

SUMMARY OF THE INVENTION

The present inventors examined affinity and action of mutants including MAX to or on various animal tissue preparations, and receptors known per se. As a result, they found, surprisingly, that although there is almost no homology between PACAP and MAX, as understood from the above amino acid sequences, MAX, and later-described NSP (SEQ ID NO: 2) and M65 (SEQ ID NO: 3) and their C-terminus amidized peptides (these referred to as a peptide represented by MAX-$NH_2$ or SEQ ID NO: 1-$NH_2$, a peptide represented by NSP-$NH_2$ or SEQ ID NO: 2-$NH_2$, and a peptide represented by M65-$NH_2$ or SEQ ID NO: 3-$NH_2$, respectively) exhibit specific affinity (or binding) to subtype receptors of type 1 among the PACAP type 1, 2 and 3 receptors.

Thus, the first embodiment of the invention provides a peptide composition for determining a subtype of PACAP receptors predicted to exist in a tissue or cells derived from a mammal, the peptide composition containing at least one peptide selected from the group consisting of peptides represented by SEQ ID NO: 1, SEQ ID NO: 1-$NH_2$, SEQ ID NO: 2, SEQ ID NO: 2-$NH_2$, SEQ ID NO: 3 and SEQ ID NO: 3-$NH_2$, and the subtype to be distinguished being PACAP type 1.

The invention of this embodiment can conveniently be utilized, for example, mainly for classification of receptors of various animal cells, and for elucidating the functions of the receptors, etc.

The second embodiment of the invention provides a method for determining a subtype of PACAP receptors predicted to exist in a tissue or cells derived from a mammal, the method comprising steps of (A) contacting the tissue or cells with at least one peptide selected from the group consisting of peptides represented by SEQ ID NO: 1, SEQ ID NO: 1-$NH_2$, SEQ ID NO: 2, SEQ ID NO: 2-$NH_2$, SEQ ID NO: 3 and SEQ ID NO: 3-$NH_2$, (B) assaying the affinity of the peptide to the tissue or cells, and (C) determining whether the subtype is PACAP type 1 or not, by assessing the specificity of the affinity.

The third embodiment of the invention provides a method for assessing the functions of PACAP type 1 receptor-expressing cells in a tissue derived from a mammal, the method comprising steps of (a) contacting a tissue or cells predicted to contain the expressing cells with at least one peptide selected from the group consisting of peptides represented by SEQ ID NO: 1, SEQ ID NO: 1-$NH_2$, SEQ ID NO: 2, SEQ ID NO: 2-$NH_2$, SEQ ID NO: 3 and SEQ ID NO: 3-$NH_2$, (b) assaying the affinity of the peptide to the tissue or cells, and (c) assessing the degree of the assayed affinity using the functions of the expressing cells as an indication.

The above process inventions will be conveniently utilized for research into the receptors, screening of agonists on PACAP type 1 receptors, etc.

The fourth embodiment of the invention provides a method for assessing the degree of disease associated with abnormalities in expression or structure of PACAP type 1 receptor in a tissue derived from a mammal, the method comprising steps of (a) contacting a tissue or cells derived from each of normal animals and a test animal and predicted to contain the expressing cells with at least one peptide selected from a group consisting of peptides represented by SEQ ID NO: 1, SEQ ID NO: 1-$NH_2$, SEQ ID NO: 2, SEQ ID NO: 2-$NH_2$, SEQ ID NO: 3 and SEQ ID NO: 3 -$NH_2$, (b) assaying the affinity of the peptide to each tissue or cells, (c) mutually comparing the affinities of the peptide to the tissues or cells, and then (d) assessing the degree of damage of the expressing cells in both kinds of said animals using the difference in the degrees of the affinities as an indication.

According to the embodiment of this invention, the states of PACAP type 1 receptors or expressing cells of the receptors can be assessed, and therefore, the invention will be utilizable for diagnosis of diseases caused by abnormality of these states.

The fifth embodiment of the invention provides a method for, in PACAP type 1 receptor-expressing cells in a mammal, heightening the cyclic AMP production ability, increasing the intracellular calcium concentration, increasing the concentration of inositol 3-phosphate, or expanding the nervous processes, which comprises a step of administering to the mammal a peptide selected from the group consisting of peptides represented by SEQ ID NO: 1, SEQ ID NO: 1-$NH_2$, SEQ ID NO: 2 and SEQ ID NO: 2-$NH_2$.

The sixth embodiment of the invention provides a method for, in PACAP type 1 receptor-expressing cells in a mammal, lowering the cyclic AMP production ability, lowering the concentration of inositol 3-phosphate, or contracting the nervous processes, which comprises a step of administering to the mammal a peptide represented by SEQ ID NO: 3 or SEQ ID NO: 3-$NH_2$.

The invention of these 5th and 6th embodiments can be utilized for prophylaxis and treatment of diseases caused by increasing or lowering of functions, particularly cyclic AMP or inositol 3-phosphate production ability, of PACAP type 1 receptor-expressing cells. As such diseases, there may be mentioned some kinds of encephalopathies, for example, Alzheimer's disease, etc., taking such specificity into account that PACAP type 1 receptors are mainly expressed in brain cells, which is different from the case of other subtype receptor(s).

DETAILED DESCRIPTION OF THE INVENTION

Figure 1:
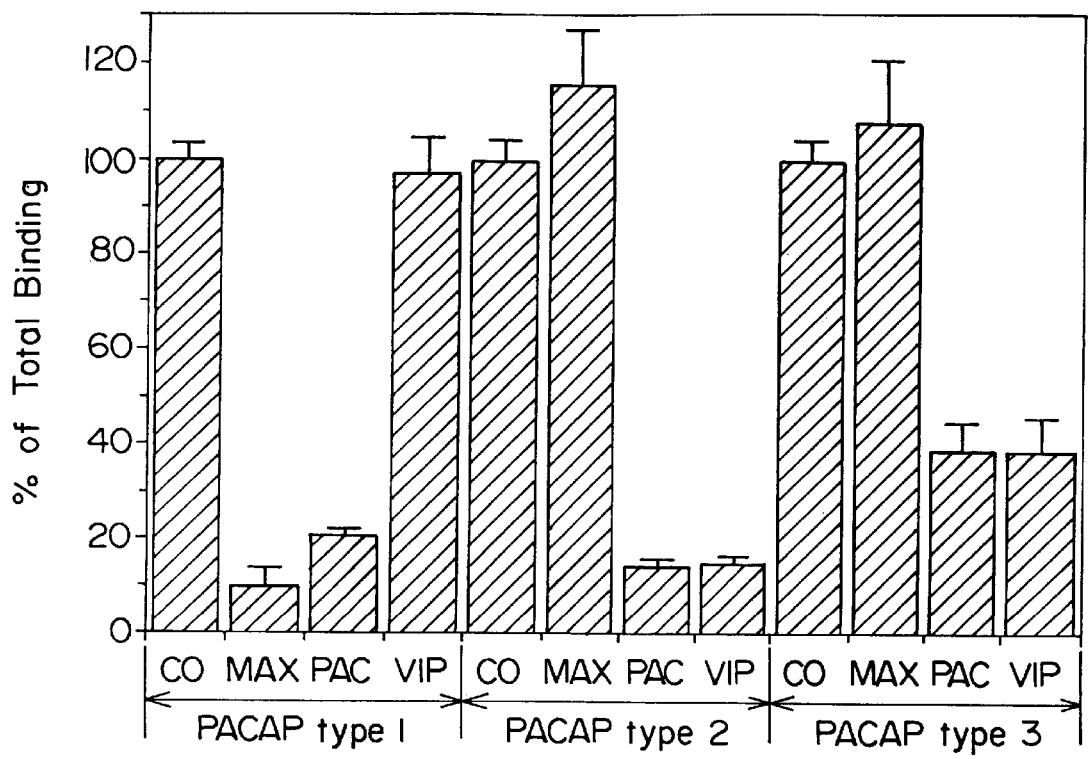
FIG. 1 is a graph showing the results of the binding assay of each peptide to each transfected COS cells. Lanes 1 to 4 are % total binding to PACAP type 1 receptor cDNA transfected COS cells, and likewise, lanes 5 to 8 are values to PACAP type 2 and lanes 9 to 12 are values to PACAP type 3. In the drawing, CO represents control, and PACAP represents PACAP 38. In lanes 1 to 4, binding of $^{125}$I MAX in the presence or absence (control) of peptides mentioned at the axis of abscissa is assayed, and in lanes 5 to 12, binding of $^{125}$I VIP is assayed.

"PACAP type 1 receptors" in the invention are membrane-bound proteins existing in encephalic tissues, particularly brain hypothalami and pituitary glands of human beings, rats, etc. Since significant difference in functions of PACAP type 1 receptors is not observed among animal species as far as the objects of the invention is concerned, PACAP type 1 receptors can be used regardless of their origins.

Cells wherein such PACAP type 1 receptors are expressed and methods for preparing the cells are known per se, are for example, described in Pisgna J. R. et al., Molecular cloning and functional expressions of the pituitary adenylate cyclase activating polypeptide type 1 receptor, *Proc. Natl. Acad. Sci. USA*, 90 (1993) 6245–6249. On the other hand, as to PACAP type 2 (VIP human type 1) and PACAP type 3 (VIP human type 2) receptors, cDNA expression vectors encoding these receptors and their expression, etc. are described, for example, in Sreedharan, S. P., et al., *Biochem. Biophys. Res. Commun.* 193 (1993) 546–553. Therefore, the receptors mentioned in the invention include not only those disclosed in these literatures, but those which are derived from other various mammals and can be prepared according to the description of these literatures.

Peptides represented by SEQ ID NO: 1 and SEQ ID NO: 1-NH$_2$ (also referred to as "MAX" and "MAX-NH$_2$", respectively. The latter means that amidation (—CONH$_2$) is made by that C-terminal amino acid residue of MAX, i.e., Lys is removed and Gly is converted to —NH$_2$. Hereinafter, analogous expressions have similar meanings) are known per se (see, U.S. Pat. No. 5,480,864). Further, peptides represented by SEQ ID NO: 2 and SEQ ID NO: 3, and SEQ ID NO: 2-NH$_2$ and SEQ ID NO: 3-NH$_2$ (referred to as NSP, M65, NSP-NH$_2$ and M65-NH$_2$, respectively), which are disclosed in U.S. Ser. No. 08/540,033 can be used.

According to the invention, MAX, MAX-NH$_2$, NSP, NSP-NH$_2$, M65 AND M65-NH$_2$ have specific affinity (or binding) to the surfaces of culture cells expressing cDNA encoding the PACAP type 1 receptor. Having specific affinity to PACAP type 1 receptors means that they do not exhibit affinity to PACAP type 2 receptors and PACAP type 3 receptors, and exhibit affinity only to PACAP type 1 receptors. Specific examples of binding conditions are described later.

Thus, according to the invention, by contacting a tissue or cells derived from a mammal with such a peptide, and assaying the binding ability of the peptide to the tissue or cells, it is possible to know whether or not PACAP type 1 receptor-expressing cells exist in the tissue or cells to be tested. Such contact is usually conducted by incubating the tissue or culture cells at temperatures having no bad influence on the cells (e.g., 4° C.) for several hours (e.g., I to 2 hours). Assay of the binding ability can be conducted by using to be used as one peptide to be used one labeled with a radioisotope (e.g., $^{125}$I, $^{13}$C and $^3$H), and measuring its binding amount by a gamma counter or the like, if necessary after an usual preliminary treatment.

Mammals mentioned in the invention include all animals regardless of their species so long as they have cells capable of expressing PACAP type 1 receptors, and as examples thereof, there can be mentioned rats, rabbits, guinea pigs, cattle, human beings, etc.

All the above-mentioned MAX, MAX-NH$_2$, NSP, NSP-NH$_2$, M65 and M65-NH$_2$ specifically bind to PACAP type 1 receptor-expressing cells, and do not bind to PACAP type 2 and PACAP type 3 receptor-expressing cells. Therefore, when a tissue or cells tested have PACAP receptors, it is possible to judge whether the receptors belong to subtype 1 or not, by assaying the binding ability of the peptides thereto, and/or assaying a form expressed when the binding information is transmitted, for example, increase of the intracellular cyclic AMP concentration, increase of the intracellular calcium concentration, increase of the inositol 3-phosphate concentration, or a change of the cellular form such as expansion of nervous processes. Further, when the binding test is conducted on cells having PACAP type 1 receptors, or a tissue or cells containing the cells, it is possible to assess functions of the receptor-expressing cells by checking the binding amount, and/or intensity of the phenotype of the information transmission. Further, by conducting the binding test on PACAP type 1 receptor-expressing cells derived from healthy (normal) animals and the expressing cells derived from a test animal, and comparing the binding amount and/or change of the phenotype of the information transmission, it is also possible to assess whether or not altered physiology exists in the expressing cells derived from the test animal or whether injury is caused or not therein.

When cells having PACAP type 1 receptors (or expression cells) are stimulated with MAX, MAX-NH$_2$, NSP or NSP-NH$_2$ according to the invention, the stimulated cells produce cyclic adenosine 3',5'-monophosphate (referred to as "cyclic AMP" or "cAMP" in the specification), and further, show the phenotypes that result from such binding and signaling. Namely, the peptides have agonistic binding ability on cells having PACAP type 1 receptors (PACAP type 1 receptor-expressing cells). Stimulation of PACAP type 1 receptor-expressing cells can usually be made by incubating the cells in medium (e.g., DMEM, HANKS) in the presence of such a peptide at a temperature of about 37° C. for 10 and several minutes (e.g., about 10 minutes). Cyclic AMP, calcium and inositol 3-phosphate produced can be detected by measuring methods known per se. For example, their measurement is conveniently conducted using, for example an Amersham cyclic AMP detection system (Amersham, Arlington Heights, Ill.).

According to the invention, since PACAP type 1 receptor-expressing cells produce cyclic AMP by stimulation with any one peptide of MAX, MAX-NH$_2$, NSP and NSP-NH$_2$, by detecting the producing ability, and/or detecting or observing the phenotype(s) of the information transmission, it is possible to determine whether or not a certain tissue or cells contain PACAP type 1 receptor-expressing cells. When this distinguishing method is combined with the assessment of affinity (or binding ability) to the cells of the mentioned peptides, it is possible to determine more accurately whether or not PACAP type 1 receptor-expressing cells exist in the tested tissue or cells.

Since MAX, MAX-NH$_2$, NSP and NSP-NH$_2$ not only do not bind to either of PACAP type 2 and PACAP type 3 receptor-expressing cells, but also do not induce production of cyclic AMP, it is possible to clearly distinguish type 1 among PACAP receptor subtypes.

Further, by combining the detection results of the cyclic AMP production ability of PACAP type 1 receptor-expressing cells based on stimulation of the expressing cells with peptide(s) such as MAX with the assessment of the binding ability of the peptide(s) to the expressing cells, it becomes possible to assess functions of the expressing cells in the tested tissue or cells more accurately. This assessment system will, for example, be useful for assessing influence which the environment, where the PACAP type 1 receptor-expressing cells are placed, has on the cells. For example, since influence which a compound has on the expression system can be examined by applying this assessment system to a competition test, it will be possible to screen novel agonists or antagonists to PACAP type 1 receptors.

Still further, when functions of PACAP type 1 receptor-expressing cells derived from healthy animals and functions of the expressing cells derived from a test animal are compared using a combination of intensity of the binding ability with intensity of the cyclic AMP production ability as a measure, it will be possible to examine more accurately whether the expressing cells derived from the test animal are normal or have some abnormality. When it is taken into account that PACAP type 1 receptor-expressing cells mainly exist in encephalic cells, the method of the invention may be utilized for diagnosis of some encephalic disorder.

According to the invention, it was found that M65 and M65-NH$_2$ antagonistically act on PACAP type 1 receptors. Namely, M65 and M65-NH$_2$ have specific binding ability to type 1 among subtypes of PACAP receptors, but do not induce cyclic AMP production of cells having the receptors. Thereby, they inhibit the binding action of MAX, MAX-NH , NSP and NSP-NH$_2$, and PACAP 38 and PACAP 27, which bind to PACAP type 1 receptor-expressing cells and induce production of cyclic AMP, to the expressing cells.

Thus, according to the invention, it is possible to assess functions and extent of injury of PACAP type 1 receptor-expressing cells, by using a combination of any of, first, binding abilities of PACAP 38 and PACAP 27, which are not specific to PACAP type 1 receptors (i.e., exhibit affinity also to type 2 and type 3), to PACAP type 1 receptor-expressing cells, and binding abilities of MAX, MAX-NH$_2$, NSP and NSP-NH$_2$ to the expressing cells with inhibition ability of M65 or M65-NH$_2$ to the binding ability as a measure. Such inhibition ability can be investigated by detecting binding ability of M65 or M65-NH$_2$ to cells to be tested, in the presence of a peptide selected from the group consisting of PACAP 38, PACAP 27, MAX, MAX-NH NSP and NSP-NH$_2$, or by detecting binding ability of PACAP 38, etc. under a reverse circumstance. In this occasion, a peptide belonging to any group is labeled with a radioisotope (e.g., $^{125}$I) and used, or alternatively, any of the above-mentioned phenotypes of the information transmission is used as an indication.

Incidentally, since PACAP was found in 1989 by Arimura et al. (*Biochem. Biophys. Res. Commun.* 164, 567–574 (1989)), it has been revealed that its actions range widely. For example, that PACAP has a nervous process expansion action (Deutsch, L. et al., *J. Biol. Chem.* 267, 5108–5113 (1992), and an action as a cell proliferation enhancer in some kind of tumor cells (Buscail, L. et al., (1992) *Gastroenterology* 103, 1002–1008). When these are taken into account, there is a possibility that MAX, MAX-NH$_2$, NSP and NSP-NH$_2$ having specificity to PACAP type 1 receptors can be used as medicaments for increasing functions of particularly encephalic cells, and M65 and M65-NH$_2$ can be used as medicaments for inhibiting the action of compounds having a bad influence on PACAP type receptor-expressing cells.

Therefore, according to the invention, it may be possible to prevent or treat diseases caused by lowering or abnormal increase of functions of the expressing cells, by administering the peptides to animals. When these peptides are administered to animals, there may be utilized a method which comprises directly injecting them, if necessary together with suitable carriers, into the affected part, or other methods usually used for administration of medicaments.

Three-letter symbols used on α-amino acids for describing the invention are based on the following abbreviations commonly used in the art.

| Common Name | Three-letter symbol |
|---|---|
| Alanine | Ala |
| Arginine | Arg |
| Asparagine | Asn |
| Aspartic acid | Asp |
| Cysteine | Cys |
| Glutamine | Gln |
| Glutamic acid | Glu |
| Glycine | Gly |
| Histidine | His |
| Isoleucine | Ile |
| Leucine | Leu |
| Lysine | Lys |
| Methionine | Met |
| Phenylalanine | Phe |
| Proline | Pro |
| Serine | Ser |
| Threonine | Thr |
| Tryptophan | Trp |
| Tyrosine | Tyr |
| Valine | Val |

EXAMPLES

The invention is illustrated below mentioning specific examples of actions of peptides, according to the invention, on PACAP type 1 receptors, and type 2 and type 3 receptors, but the true scope is now particularly pointed out in the appended claims.

Materials and Methods

Peptides: MAX (SEQ ID NO: 1) and MAX-NH$_2$ were prepared according to U.S. Pat. No. 5,480,864. NSP (SEQ ID NO: 2) and NSP-NH$_2$, and M65 (SEQ ID NO: 3) and M65-NH$_2$ were prepared according to the method described in U.S. Ser. No. 08/540,033. These peptides can also be prepared by peptide synthesis based on the disclosed sequences. Labeling of these peptides with $^{125}$I was conducted by Amersham custom labeling service department (specific activity on each peptide: about 2000 Ci/mmol). PACAP 38 (SEQ ID NO: 4-NH$_2$), PACAP 27 (SEQ ID NO: 5-NH$_2$), PACAP 6-38 (SEQ ID NO: 6-NH$_2$) and PACAP 6-27 (SEQ ID NO: 7-NH$_2$), and GRF, glucagon, secretin and PHI were purchased from Peninsula (Belmont, Calif.). Further, iodinated PACAP 27 and VIP were purchased from Dupont and Amersham, respectively.

Receptor: PACAP rat type 1 cDNA was obtained from Dr. Joseph R. Pisegna, National Institute of Diabetes, Digestive and Kidney Diseases, NIH. PACAP human type 2 and type 3 (VIP human type 1 and type 2) cDNA were obtained from Dr. Sunil P. Sreedharan, Division of Allergy & Immunology, UCSF.

Transfection with cDNA

COS cells were sown one day before transfection in 6-well dishes containing complete DMEM medium (DMEM with 10% FCS, penicillin and streptomycin). COS cells in wells were transfected with each cDNA, respectively, according to a DEAE-dextran method using standard procedure. These cells were incubated at 37° C. for 3 hours, and then the medium in each well was removed. These cells were treated with 10% dimethyl sulfoxide (DMSO) in complete DMEM medium for 2.5 minutes. After removal of the 10% DMSO solution, a completely fresh medium was added, and 3 days later, these cells were used for assay.

Binding of Peptides

Proliferated cells of the PACAP type 1, type 2 and type 3 receptor-expressing cells, prepared as above, were incubated together with each peptide as follows at 4° C. for 2 hours, and then binding amounts of the peptides to the cells were measured.

(1) Each confluent transfected cells on the 6-well plates were contacted with each peptide by incubating the cells in a medium (DMEM) in the presence or absence of 1 μM of unlabeled MAX, PACAP 38 or VIP at 4° C. for 2 hours using 70 pM [$^{125}$I]MAX for PACAP type 1 transfected cells, and 70 pM each of [$^{125}$I] VIP for PACAP type 2 and type 3 transfected cells. At the end of incubation, each of the resultant broths was filtered under reduced pressure by passing it through a GF/C Whatman glass microfiber filter pretreated with 0.5% polyethylene-imine. Each cell culture was washed three times with 3 ml portions of the medium at 4° C. The radioactivity trapped on each filter was measured using a gamma counter (MINIGAMMA (LKB-Wallac, Turku, Finland)). Each measured values were recorded as a mean value (mean±standard deviation) in tripricate determinations of binding amounts of each labeled peptide to the type 1 transfected cells. The results of % total binding obtained by making conversion thereof supposing the total binding in the case where any unlabeled peptide does not exist (control) to be 100% total binding are shown in FIG. 1.

It is understood from FIG. 1 that MAX has specific affinity to PACAP type 1 receptors.

Figure 2:
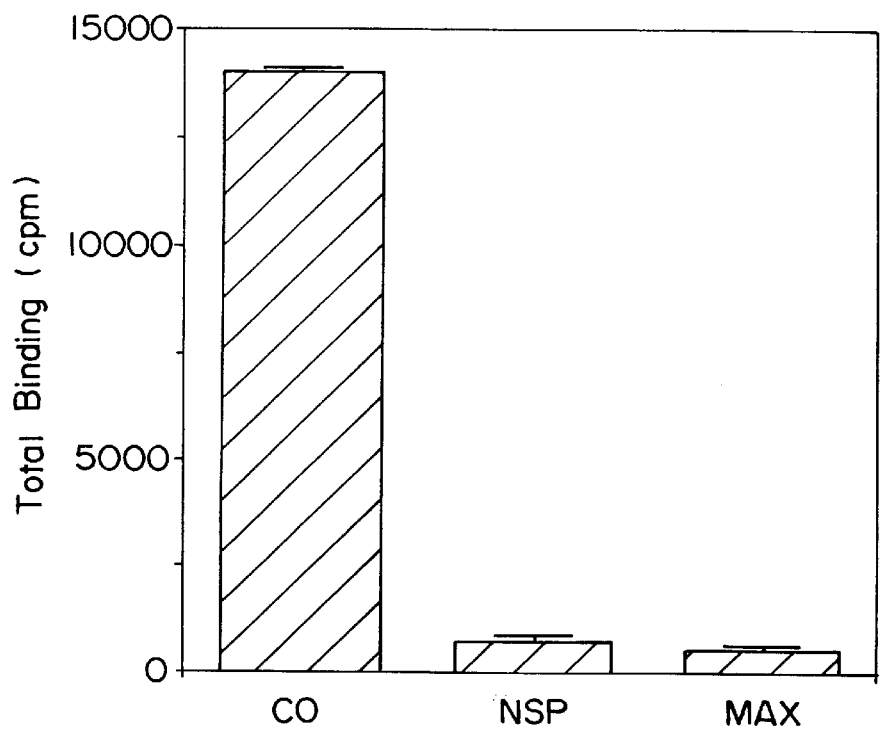
FIG. 2 is a graph showing the results of the binding assay of NSP and MAX to PACAP type 1 receptor cDNA transfected COS cells. CO is total binding (control) of labeled MAX in the absence of peptides.

(2) Binding assay of NSP to PACAP type 1 receptor cDNA transfected cells was conducted in the same manner as in the above (1). Binding of 70 pM [$^{125}$I] NSP to the COS cells was measured in the presence or absence (control) of 1 μM of NSP or MAX as an unlabeled peptide. The results are shown in FIG. 2. Values are means i standard deviations of triplicate determinations.

It is understood from FIG. 2 that NSP exhibits binding to PACAP type 1 receptors almost equal to that of MAX.

(3) % of total binding of 70 pM [$^{125}$I]MAX (PACAP type 1 transfected cells) or 70 pM [$^{125}$I]VIP (PACAP type 2 and 3 transfected cells, respectively) was measured in the presence of 1 μM peptides (M65, PACAP 6-38 and MAX for type 1; M65, PACAP 6-38 and PACAP 38 for types 2 and 3) in place of MAX, PACAP 38 and VIP in the above (1). The measured values were recorded as relative mean values calculated when the measurement result in the absence of the peptides (control) was supposed to be 100%. Values are means±standard deviations of triplicate determinations. The results are shown in FIG. 3.

Figure 3:
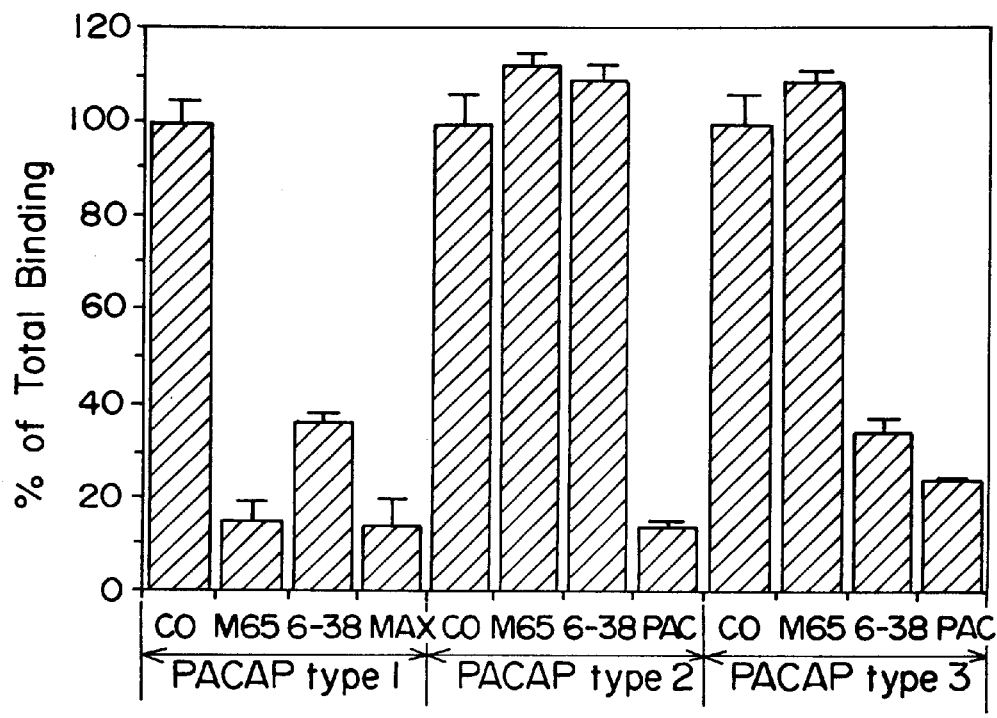
FIG. 3 is a graph showing the assay results of % of total binding to each transfected COS cells of M65, PACAP 6-38, MAX and PACAP 38. As to PACAP type 1, binding of [$^{125}$I]PACAP 27 in the presence or absence (control) of peptides mentioned at the axis of abscissa is shown, and as to PACAP types 2 and 3, binding in the presence or absence (control) of each peptide mentioned at the axis of abscissa is shown. CO, 6-38 and PAC mean control, PACAP 6-38 and PACAP 38, respectively.

It is seen from FIG. 3 that M65 exhibits binding to PACAP type 1 receptors equal to that of MAX.

Measurement of Cyclic AMP

In the same manner as above, COS cells transfected with each cDNA were proliferated up to confluence in 24-well plates each containing HANKS medium with 1 mM 3-isobutyl-1-methyl xanthine and 0.1% bovine serum albumin (BSA). Then, the proliferated cells were stimulated by incubating them together with 100 nM each of the peptides at 37° C. for 10 minutes. The test wherein no peptide was used was used as control. The incubation was terminated by aspiration of the medium and addition of 400 μl ice-cold 50 mM Tris, 4 mM EDTA, pH 7.5. The cells were harvested and transferred to 1.5-ml Eppendorf tubes. The cells were boiled therein for 5 minutes and then spined for 5 minutes. The supernatants were collected and 50 μl aliquots were taken for assay of cyclic AMP using Amersham cyclic AMP detection system.

Figure 4:
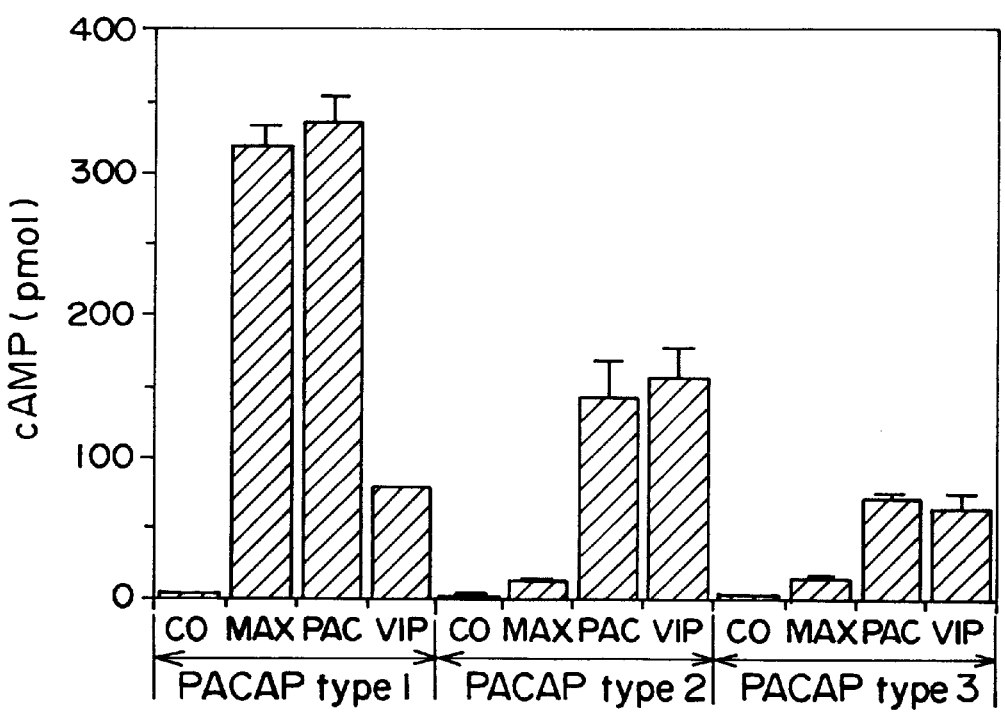
FIG. 4 is a graph showing the assay results of cyclic AMP production in each transfected cells caused by stimulation with each peptide. The values are values on peptides mentioned at the axis of abscissa of the respective transfected cells. In the drawing, CO and PAC mean control and PACAP 38, respectively.

(1) The results of stimulation of PACAP type 1 receptor cDNA transfected cells with MAX, PACAP 38 and VIP (lanes 1–4), and the results of stimulation of PACAP type 1 and 2 receptor cDNA transfected COS cells with each peptide (lanes 5–8 and 9–12. control does not contains any peptide) were shown in FIG. 4. Values are means±standard deviations of triplicate determinations.

Figure 5:
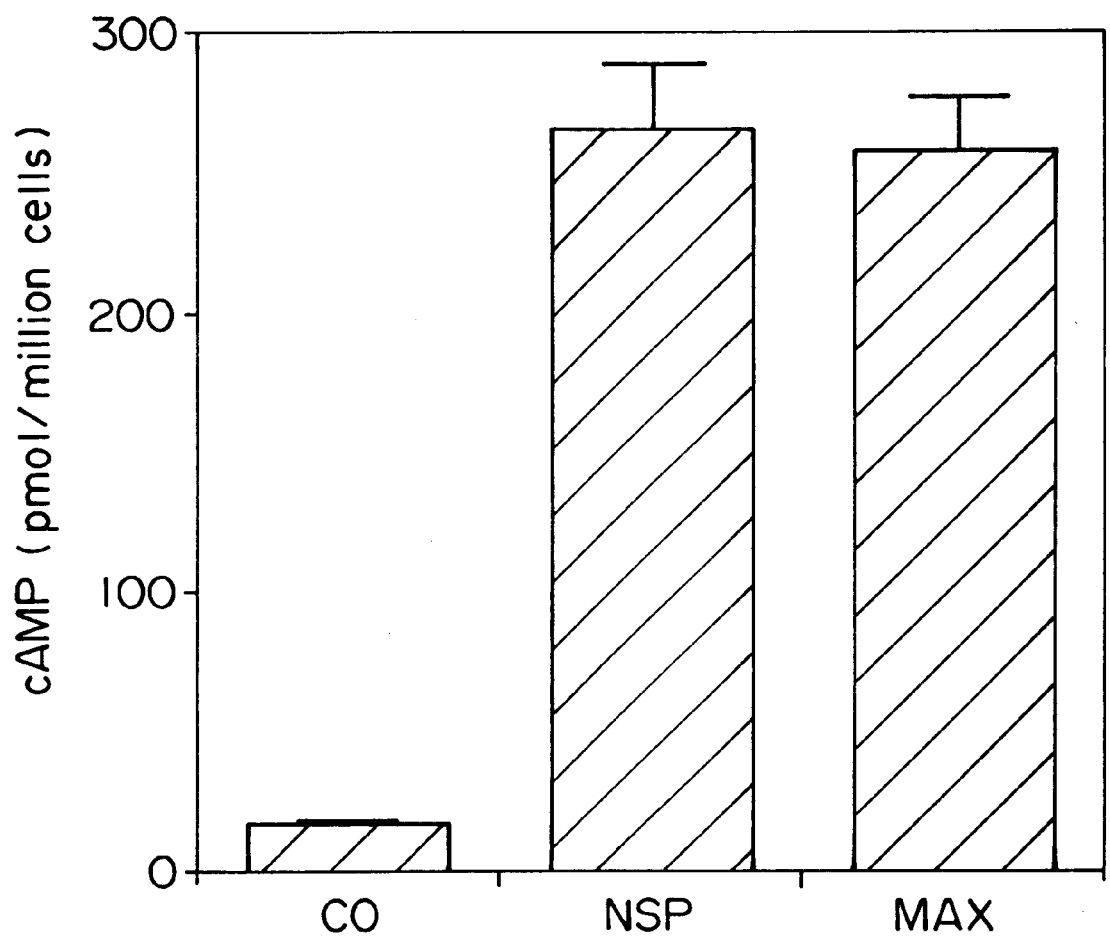
FIG. 5 is a graph showing the assay results of cyclic AMP production of PACAP type 1 receptor cDNA transfected COS cells caused by MAX and NSP.

(2) Cyclic AMP production in PACAP type 1 cDNA transfected COS cells using MAX and NSP was assayed in the same manner as in the above (1). The results are shown in FIG. 5.

It is seen from FIG. 4 that MAX brings about cyclic AMP production by PACAP type 1 receptor cDNA transfected cells almost equal to that brought about by PACAP 38, but does not induce cyclic AMP production by type 2 and 3 receptor cDNA transfected cells, although PACAP 38 brings about cyclic AMP production by the type 2 and 3 cells equal to that brought about by VIP. It is seen from FIG. 5 that NSP brings about cyclic AMP production characteristics equal to that brought about by MAX.

Blocking Effect of M65 and PACAP 38 on the PACAP 38 Stimulated Cyclic AMP Production Blocking effect of M65 and PACAP 6-38 on PACAP 38 stimulated cyclic AMP production in PACAP type 1, type 2 and type 3 receptor cDNA transfected COS cells was assayed.

Figure 6:
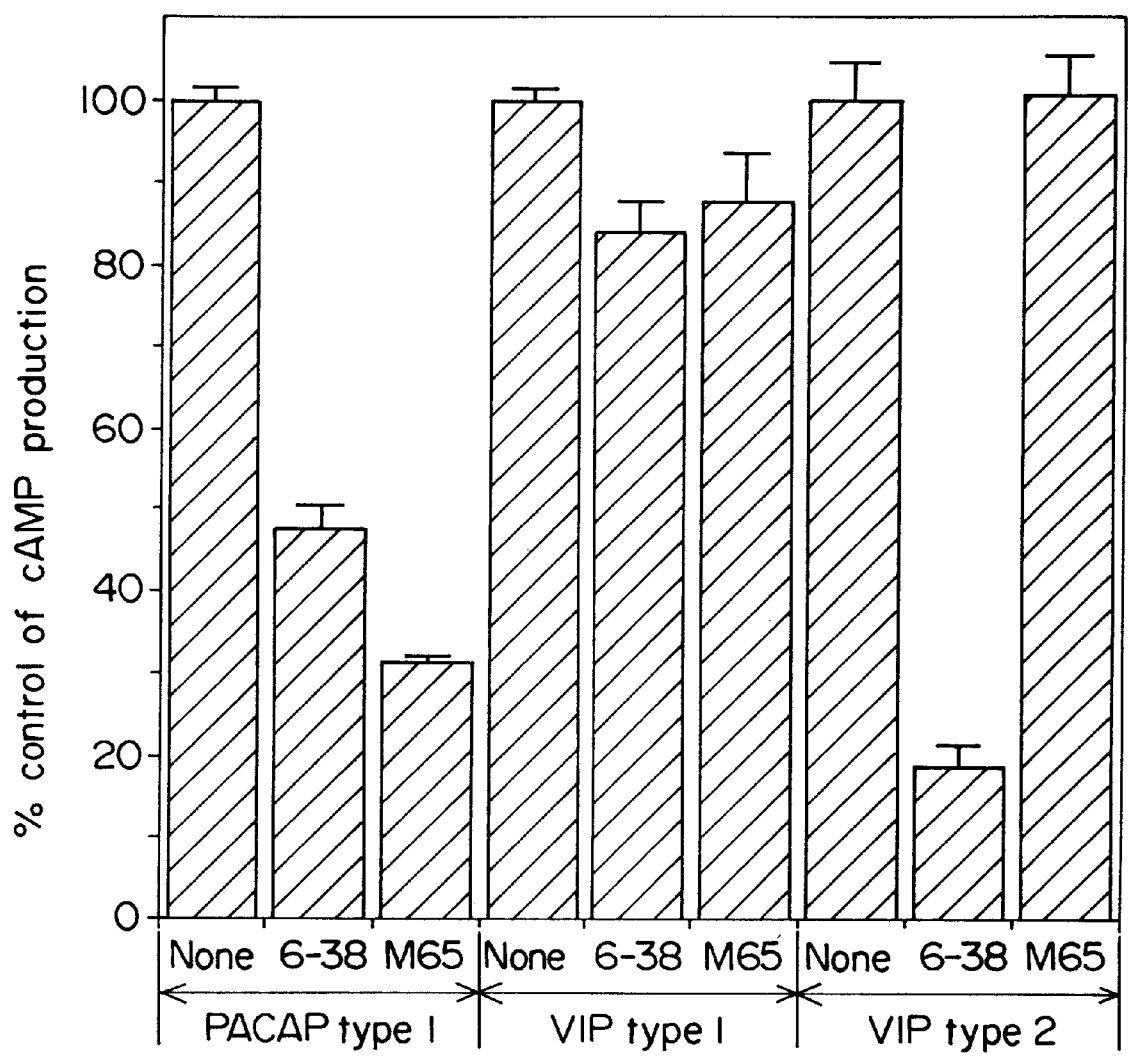
FIG. 6 is a graph showing the blocking effects of M65 or PACAP 6-38 on PACAP 38-stimulated cyclic AMP production. In the drawing, values on PACAP type 1 receptor cDNA transfected COS cells are shown in lanes 1 to 3, and values on type 2 and type 3 COS cells are shown in lanes 4 to 6 and lanes 7 to 9, respectively.

The transfected COS cells were incubated together with 1 nM PACAP 38 at 37° C. for 10 minutes in the presence of 10 μM M65 or PACAP 6-38, and cyclic AMP production of each cells was assayed. Assay of cyclic AMP was conducted by Amersham cyclic AMP detection system. Relative cyclic AMP production was recorded obtained when the result in the absence of M65 or PACAP 6-38 (control) was supposed to be 100%. The results are shown in FIG. 6. Values are means±standard deviations of duplicate determinations.

It is seen from FIG. 6 that, as to blocking effect of peptides on PACAP 38 stimulated cyclic AMP production, M65 exhibits stronger blocking on PACAP type 1 receptor cDNA transfected COS cells than PACAP 6-38 which is an antagonist of PACAP 38, but does not substantially block cyclic AMP production by the type 3 receptor cDNA transfected COS cells.

As understood from the above, M65 seems to act as a specific antagonist to PACAP type 1 receptors of PACAP 38.

It is ascertained that MAX-NH$_2$, NSP-NH$_2$ and M65-NH$_2$ corresponding to MAX, NSP and M65, respectively, have the same actions as mentioned above.

Inhibition of Specific Binding of [$^{125}$I]MAX and [$^{125}$I]PACAP 27 to Rat Brain (1) Preparation of Membranes Rat brain tissue from which the cerebellum was removed was placed in 10 volumes of ice-cold 50 mM Tris-HCl buffer (pH 7.6) containing 0.32 M sucrose, 5 mM EDTA, 1 μg/ml leupeptin, 1 μg/ml pepstatin A, 2 μg/ml bacitracin and 10 μg/ml phenylmethylsulfonyl fluoride. The tissue was homogenized with a plytron PT 3000 (Brinkmann Instruments, Westbury, N.Y.) for 30 seconds at power level 7 at 4° C. The homogenate was centrifuged for 10 minutes at 1,000×g at 4° C. The supernatant was removed, and the pellet was resuspended in 15 ml of homogenizing buffer and homogenized again using the Polytron at the same setting as the first homogenization, and the homogenate was centrifuged at 1,000×g for 10 minutes at 4° C. The combined supernatant was centrifuged at 30,000×g for 45 minutes at 4° C. The pellet was washed two times by successive resuspension in 50 mM Tris-HCl buffer containing 1 mM MgCl$_2$, 0.3% BSA, 1 μg/ml leupeptin, 1 μg/ml pepstatin A, 2 μg/ml bacitracin and 10 μg/ml phenylmethylsulfonyl fluoride.

(2) Binding of [$^{125}$I]MAX and PACAP 27

Figure 7:
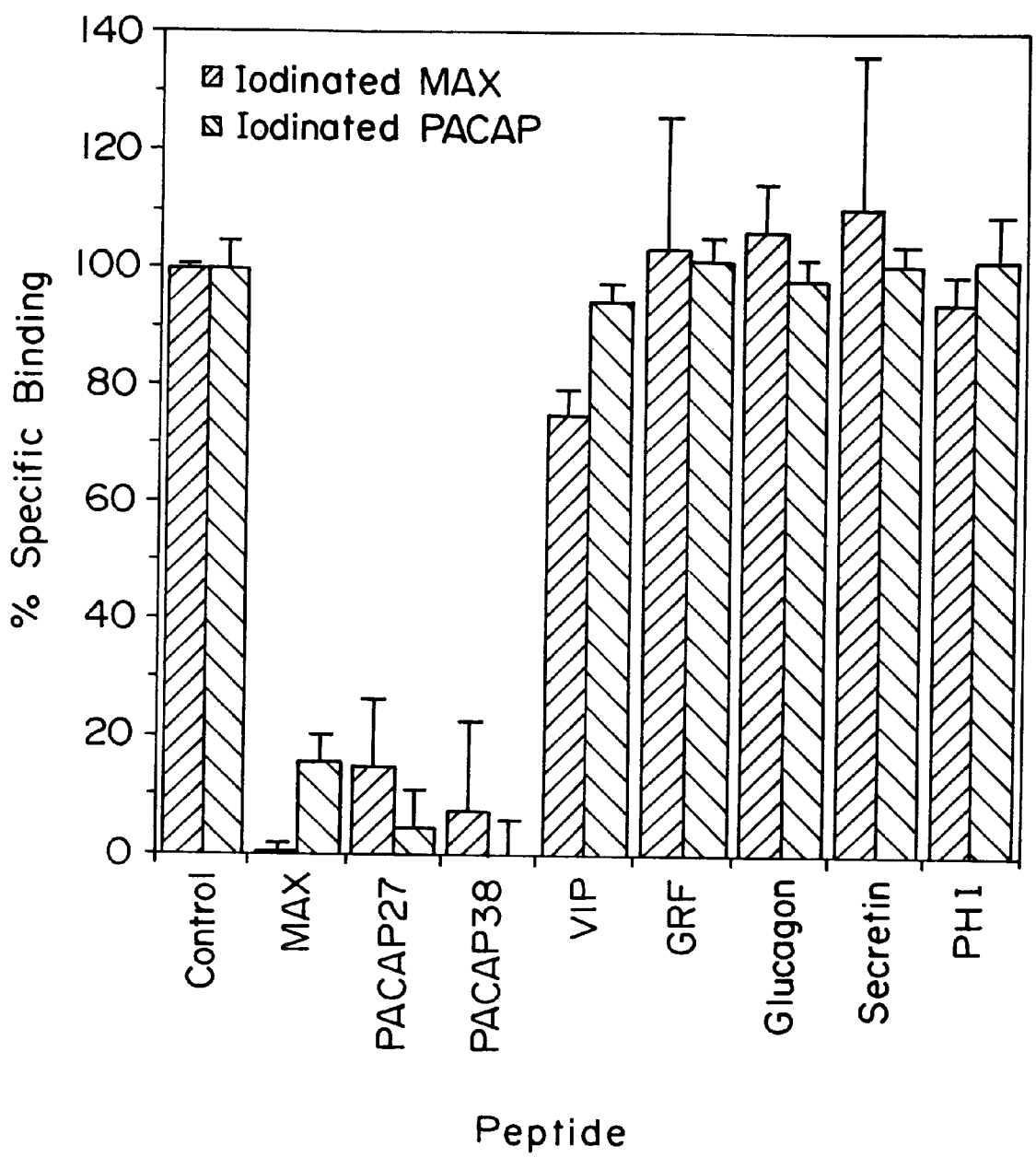
FIG. 7 is a graph showing the inhibition ability of MAX and secretin family peptides on specific binding of MAX and PACAP 27 on the rat brain crude membrane. The values show % of specific binding of [$^{125}$I]MAX and [$^{125}$I]PACAP 27 in the presence of peptides mentioned at the axis of abscissa.

Crude membranes (250–400 μg) were incubated for 1 hour at 22° C. in a final volume of 0.5 ml consisting of 50 mM Tris-HCl buffer (pH 7.6) containing 0.3% BSA, 1 mM MgCl$_2$, 1 μg/ml leupeptin, 1 μg/ml pepstatin A, 2 μg/ml bacitracin, 10 μg/ml phenylmethylsulfonyl fluoride and 50 pM [$^{125}$I]MAX in the absence or presence of 1 μM MAX. At the end of incubation, samples were assayed for protein-bound radioactivity by vacuum filtration through GF/C Whatman glass microfiber filters pretreated with 0.5% polythlenimine. Filters were then washed with 3×3 ml of incubation buffer at 4° C. The radioactivity trapped on the filters was measured using a gamma counter. Non-specific [$^{125}$I] MAX and PACAP 27 binding was determined by the addition of 1 μM unlabeled MAX, PACAP 38, PACAP 27, VIP, GRF, glucagon, secretin and PHI, respectively. In the results, specific binding (total cpm minus non-specific cpm) is shown. Proteins or peptides were estimated by the method of Bradford using bovine serum albumin as standard. The results are shown in FIG. 7. Values are means±standard deviations of triplicate determinations.

It is seen from FIG. 7 that any of secretin family peptides other than PACAP 27 and PACAP 38 does not inhibit either specific [$^{125}$I]MAX or [$^{125}$I]PACAP 27 binding to rat brain.

(3) The ligand specificity of the rat brain PACAP receptor (or MAX receptor) was investigated by analyzing competition ability of various peptides, i.e., MAX, M65, PACAP 38, PACAP 27, PACAP 6-38, PACAP 6-27 and VIP with [$^{125}$I]MAX and [$^{125}$I]PACAP binding, according to the binding assay of the above (2). Displacement patterns on [$^{125}$I]MAX and [$^{125}$I]PACAP 27 were analogous. IC$_{50}$ values on the various peptides are shown in the following Table 1.

TABLE 1

Relative affinites of the PACAP receptor in rat brain crude membrane for various peptides

| Peptide | [$^{125}$I] MAX | [$^{125}$I] PACAP 27 |
| --- | --- | --- |
| MAX | 1.14 ± 0.07 | 3.35 ± 0.29 |
| M65 | 2.96 ± 0.54 | 5.96 ± 0.71 |
| PACAP 38 | 1.91 ± 0.13 | 4.45 ± 0.22 |
| PACAP 6-38 | 8.35 ± 2.04 | 39.14 ± 3.00 |
| PACAP 27 | 2.16 ± 0.45 | 9.55 ± 0.75 |
| PACAP 6-27 | 234.6 ± 56.2 | 1031.3 ± 63.0 |

It is seen from Table 1 that the affinity of M65, an antagonist of MAX, is very close to the affinity of PACAP agonists (e.g., MAX, PACAP 27 and PACAP 38). PACAP 6-38, a PACAP antagonist, exhibits IC$_{50}$ values of 8.35 nM and 35.14 nM on [$^{125}$I]MAX and [$^{125}$I]PACAP 27, respectively, and these values are about 6–10 times higher than the values exhibited by M65. IC$_{50}$ of PACAP 6-27 is much higher than the value by M65. These data shows a possibility that M65 is very useful as a PACAP type 1 specific antagonist.

What is claimed is:

1. A method for assessing the signal transduction ability of pituitary adenylate cyclase activating polypeptide ("PACAP") type 1 receptor-expressing cells in a tissue derived from a mammal, the method comprising steps of (a) contacting a tissue or cells predicted to contain the expressing cells with at least one peptide selected from the group consisting of peptides represented by SEQ ID NO: 1, SEQ ID NO: 1-NH$_2$, SEQ ID NO: 2, SEQ ID NO: 2-NH$_2$, SEQ ID NO: 3 AND SEQ ID NO: 3-NH$_2$, (b) assaying the affinity of the peptide to the tissue or cells, and (c) assessing the degree of the assayed affinity using the signal transduction ability of expressing cells as an indicator.

2. A method for assessing the signal transduction ability of PACAP type 1 receptor-expressing cells in a tissue derived from a mammal, the method comprising steps of stimulating a tissue or cells predicted to contain the expressing cells with a peptide selected from the group consisting of peptides represented by SEQ ID NO: 1, SEQ ID NO: 1-NH$_2$, SEQ ID NO: 2 and SEQ ID NO: 2-NH$_2$, and then on the stimulated expressing cells, either detecting the cyclic adenosine monophosphate ("cyclic AMP") production ability, detecting the intracellular calcium concentration, detecting inositol 3-phosphate, or observing a change of the cellular form.

3. A method according to claim 2 which further comprises a combination of steps of stimulating the tissue or cells with a peptide selected from the group consisting of peptides represented by SEQ ID NO: 1, SEQ ID NO: 1-NH$_2$, SEQ ID NO: 2, SEQ ID NO: 2-NH$_2$, SEQ ID NO: 4-NH$_2$ and SEQ ID NO: 5-NH$_2$, and then on the stimulated expressing cells, either detecting the cyclic AMP production ability, detecting the intracellular calcium concentration, detecting inositol 3-phosphate, or observing a change of the cellular form with steps of conducting the stimulation by stimulating the tissue or cells with such a system that a peptide represented by SEQ ID NO: 3 or SEQ ID NO: 3-NH$_2$ is further added, and then on the stimulated expressing cells, either detecting the cyclic AMP production ability, detecting the intracellular calcium concentration, detecting inositol 3-phosphate, or observing a change of the cellular form.

4. A method for assessing the degree of abnormalcy of PACAP type 1 receptor-expressing cells in a tissue derived from a mammal, the method comprising steps of (a) contacting a tissue or cells derived from each of normal animals and a test animal and predicted to contain the expressing cells with at least one peptide selected from the group consisting of peptides represented by SEQ ID NO: 1, SEQ ID NO: 1-NH$_2$, SEQ ID NO: 2, SEQ ID NO: 2-NH$_2$, SEQ ID NO: 3 and SEQ ID NO: 3-NH$_2$, (b) assaying the affinity of the peptide to each tissue or cells, (c) mutually comparing the affinities of the peptide to the tissues or cells, and then (d) assessing the degree of damage of the expressing cells in both kinds of said animals using the difference in the degrees of the affinities as an indicator.

5. A method for assessing the degree of abnormalcy of PACAP type 1 receptor-expressing cells in a tissue derived from a mammal, the method comprising steps of stimulating a tissue or cells derived from each of normal animals and a test animal and predicted to contain the expressing cells with a peptide selected from the group consisting of peptides represented by SEQ ID NO: 1, SEQ ID NO: 1-NH$_2$, SEQ ID NO: 2 and SEQ ID NO: 2-NH$_2$, and then on the stimulated expressing cells, either detecting the cyclic AMP production ability, detecting the intracellular calcium concentration, detecting inositol 3-phosphate, or observing a change of the cellular form and a step of comparing both kinds of said animals in cyclic AMP production ability.

6. A method according to claim 5 which further comprises a combination of steps of stimulating each tissue or cells with a peptide selected from the group consisting of peptides represented by SEQ ID NO: 1, SEQ ID NO: 1-NH$_2$, SEQ ID NO: 2, SEQ ID NO: 2-NH$_2$, SEQ ID NO: 4-NH$_2$ and SEQ ID NO: 5-NH$_2$, and then on the stimulated expressing cells, either detecting the cyclic AMP production ability, detecting the intracellular calcium concentration, detecting inositol 3-phosphate, or observing a change of the cellular form steps of conducting the stimulation by stimulating the tissue or cells with such a system that a peptide represented by SEQ ID NO: 3 or SEQ ID NO: 3-NH$_2$ is further added, and then on the stimulated expressing cells, either detecting the cyclic AMP production ability, detecting the intracellular calcium concentration, detecting inositol 3-phosphate, or observing a change of the cellular form and a step of comparing and examining the results of the detection or observation.

7. A method according to claim 4 or 5 wherein the mammal is a human being.

8. A method for, in PACAP type 1 receptor-expressing cells in a mammal, lowering the cyclic AMP production ability, lowering the concentration of inositol 3-phosphate, or contracting the nervous processes, which comprises a step of administering to the mammal a peptide represented by SEQ ID NO: 3 or SEQ ID NO: 3-NH$_2$.

9. A method according to claim 8 wherein the mammal is a human being.

10. A peptide composition comprising at least one peptide selected from the group consisting of SEQ ID NO: 3 and SEQ ID NO: 3-NH$_2$, and a medium used in the culturing of cells.

11. The peptide composition according to claim 10, which comprises the peptide according to SEQ ID NO: 3 or SEQ ID NO: 3-NH$_2$, and a peptide selected from the group consisting of SEQ ID NO: 1, SEQ ID NO: 1-NH$_2$, SEQ ID NO: 2 and SEQ ID NO: 2-NH$_2$.

12. A method for determining whether or not a tissue or cell derived from a mammal contains a subtype 1 of a PACAP receptor, the method comprising steps of:

(A) contacting the tissue or cell with at least one peptide selected from the group consisting of SEQ ID NO: 1, SEQ ID NO: 1-NH$_2$, SEQ ID NO: 2, SEQ ID NO: 2-NH$_2$, SEQ ID NO: 3 and SEQ ID NO: 3-NH$_2$, and (B) assaying the affinity of the peptide to the tissue or cell to determine whether or not the PACAP receptor is subtype 1.

13. A method for determining a subtype of PACAP receptor predicted to exist in a tissue or cell derived from a mammal, the method comprising steps of:

(A) contacting the tissue or cell with at least one peptide selected from the group consisting of peptides represented by SEQ ID NO: 1, SEQ ID NO: 1-NH$_2$, SEQ ID NO: 2, SEQ ID NO: 2-NH$_2$, SEQ ID NO: 3 and SEQ ID NO: 3-NH$_2$, (B) assaying the affinity of the peptide to the tissue or cell, and (C) determining whether or not the PACAP receptor is subtype 1, by assessing the specificity of the affinity.

14. The method according to claim 12 or 13 which further comprises steps of:

stimulating the tissue or cell with a peptide selected from the group consisting of SEQ ID NO: 1, SEQ ID NO: 1-NH$_2$, SEQ ID NO: 2 and SEQ ID NO: 2-NH$_2$ and detecting a concentration of cyclic AMP, intracellular calcium or inositol 3-phosphate in the tissue or cell, or observing a change in cellular form.

15. The method according to claim 12 or 13 which further comprises steps of:

stimulating the tissue or cell with a peptide selected from the group consisting of SEQ ID NO: 1, SEQ ID NO: 1-NH$_2$, SEQ ID NO: 2, SEQ ID NO: 2-NH$_2$, SEQ ID NO: 4-NH$_2$ and SEQ ID NO: 5-NH$_2$, detecting a cyclic AMP ("cyclic AMP") concentration of the stimulated tissue or cell, further adding a peptide according to SEQ ID NO: 3 or SEQ ID NO: 3 -NH$_2$, and detecting a concentration of cyclic AMP, intracellular calcium or inositol 3-phosphate in the tissue or cell, or observing a change in cellular form.

16. The method according to claim 14, wherein the change in cellular form is expansion of nervous processes.

17. The method according to claim 15, wherein the change in cellular form is expansion of nervous processes.

* * * * *